(12) United States Patent
Wunderle et al.

(10) Patent No.: US 8,337,565 B2
(45) Date of Patent: Dec. 25, 2012

(54) HIP-JOINT PROSTHESIS

(75) Inventors: Dirk Wunderle, Zürich (CH); Alex Seidl, Zürich (CH)

(73) Assignee: Smith and Nephew Orthopaedics AG, Rotkreuz (CH)

( * ) Notice: Subject to any disclaimer, the term of this patent is extended or adjusted under 35 U.S.C. 154(b) by 261 days.

(21) Appl. No.: 12/778,866

(22) Filed: May 12, 2010

(65) Prior Publication Data

US 2011/0282462 A1    Nov. 17, 2011

Related U.S. Application Data

(63) Continuation-in-part of application No. 12/067,635, filed as application No. PCT/EP2006/007842 on Aug. 8, 2006.

(30) Foreign Application Priority Data

Sep. 20, 2005 (DE) .......................... 10 2005 044 872
Oct. 12, 2005 (DE) .......................... 10 2005 048 873

(51) Int. Cl.
*A61F 2/36* (2006.01)
(52) U.S. Cl. ........................................ 623/22.11; 703/7
(58) Field of Classification Search .............. 623/22.11, 623/22.12, 23.35; 606/443, 449; 600/410, 600/416; 703/7
See application file for complete search history.

(56) References Cited

U.S. PATENT DOCUMENTS

| 4,506,393 | A | * | 3/1985 | Murphy | 128/898 |
| 4,908,035 | A | | 3/1990 | Deckner et al. | |
| 5,290,318 | A | * | 3/1994 | Ling et al. | 623/23.38 |
| 7,749,278 | B2 | * | 7/2010 | Frederick et al. | 623/22.41 |
| 2002/0177901 | A1 | * | 11/2002 | Howie | 623/23.35 |
| 2006/0276904 | A1 | * | 12/2006 | Zweymuller | 623/22.11 |
| 2009/0036994 | A1 | | 2/2009 | Moser et al. | |

* cited by examiner

*Primary Examiner* — Thomas J Sweet
*Assistant Examiner* — Christopher D Prone
(74) *Attorney, Agent, or Firm* — Krieg DeVault LLP

(57) ABSTRACT

A method of optimizing the geometry of a femoral stem of hip joint prosthesis is disclosed. The femoral stem comprises a neck and an anchoring blade that is attached to the neck and that tapers towards a distal end with a lateral narrow side comprising a distal straight portion and a proximal arcuate portion corresponding to a curve. The transition between the distal straight portion and the proximal arcuate portion occurs at an outer lateral point. The method comprises a means of optimizing the profile of the curve of said proximal arcuate portion by a process of iterative modeling steps using a series of curves each defined by a path traced by the outer lateral point on withdrawal of a profile of the stem from a cavity of complementary shape to the stem.

15 Claims, 5 Drawing Sheets

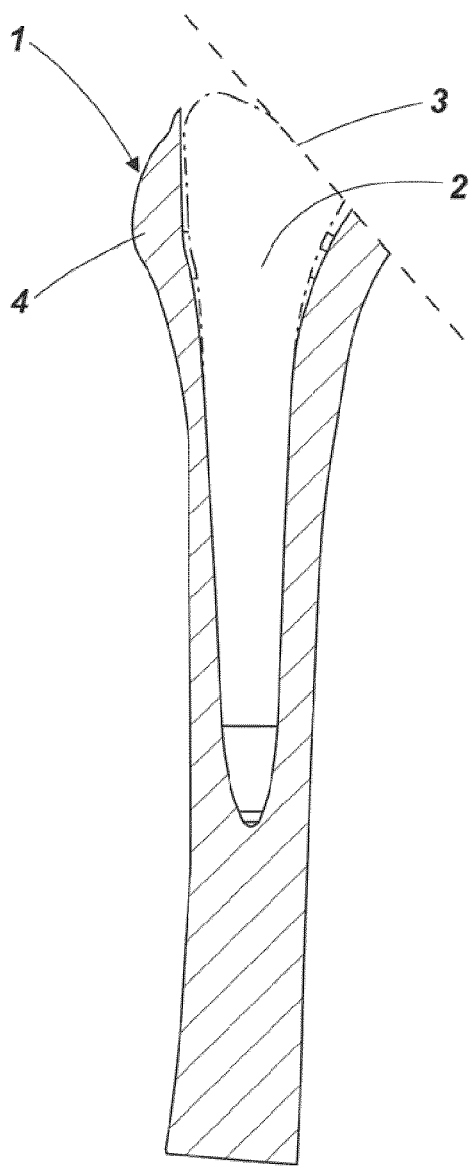
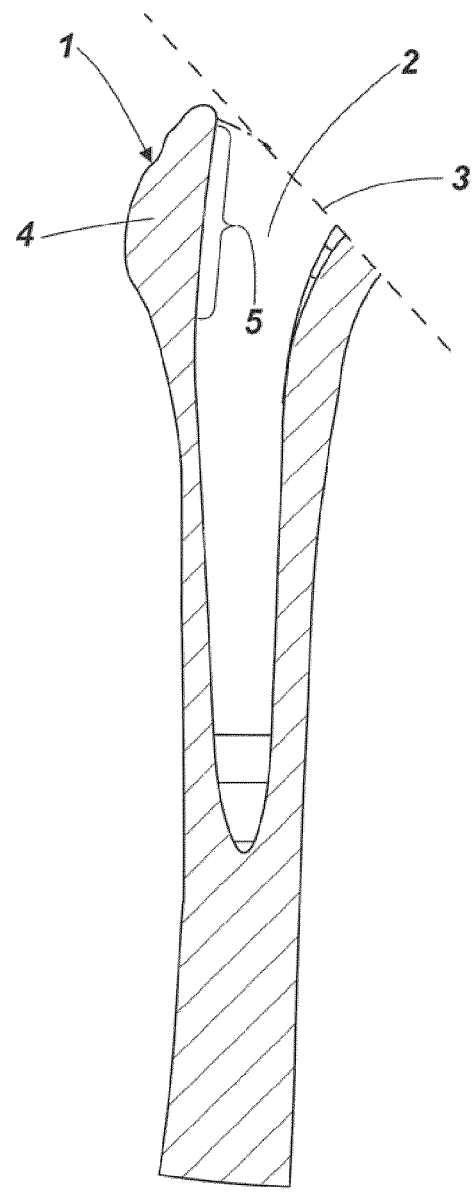
*Fig. 1*
(PRIOR ART)
*Fig. 2*

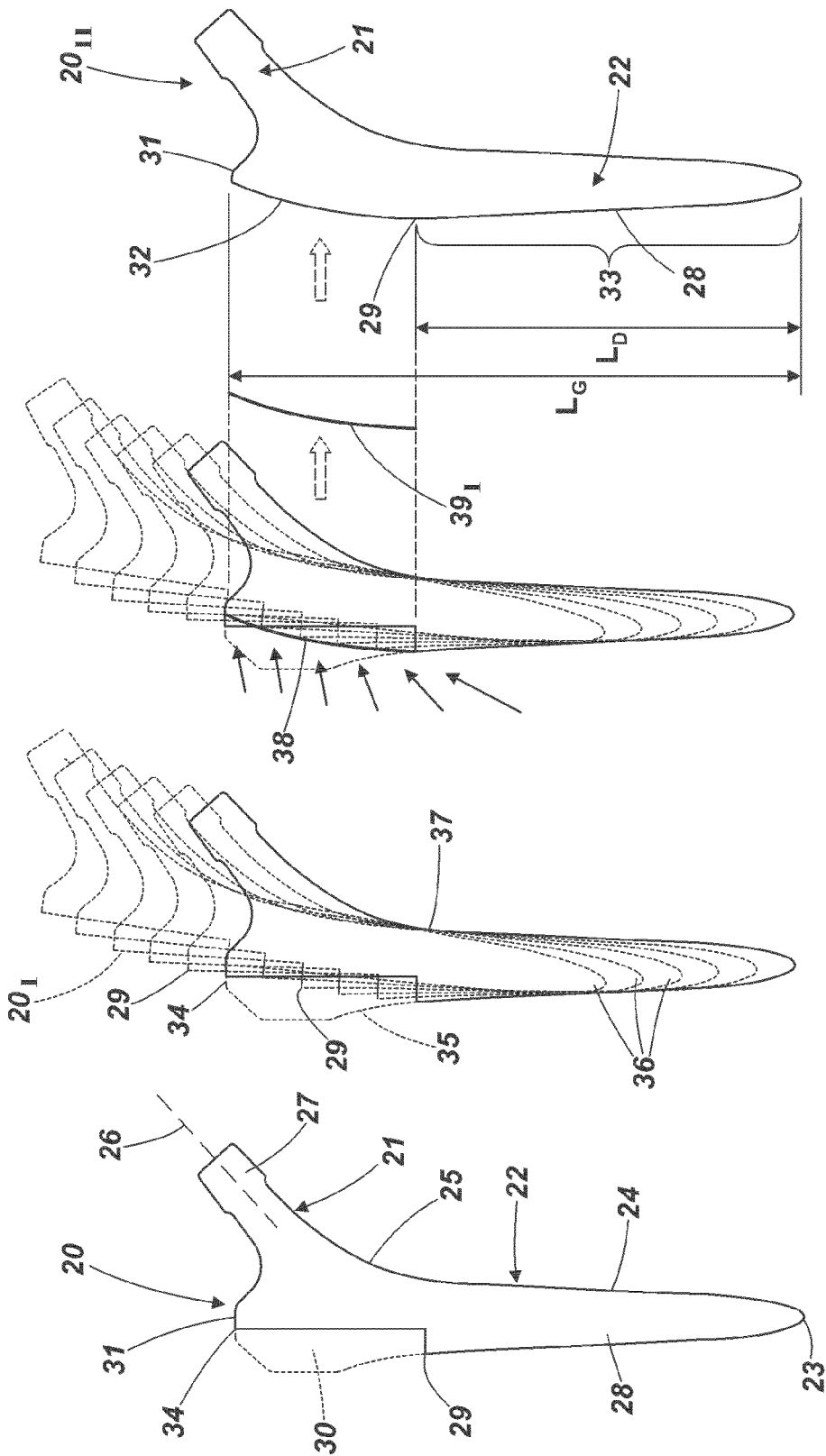

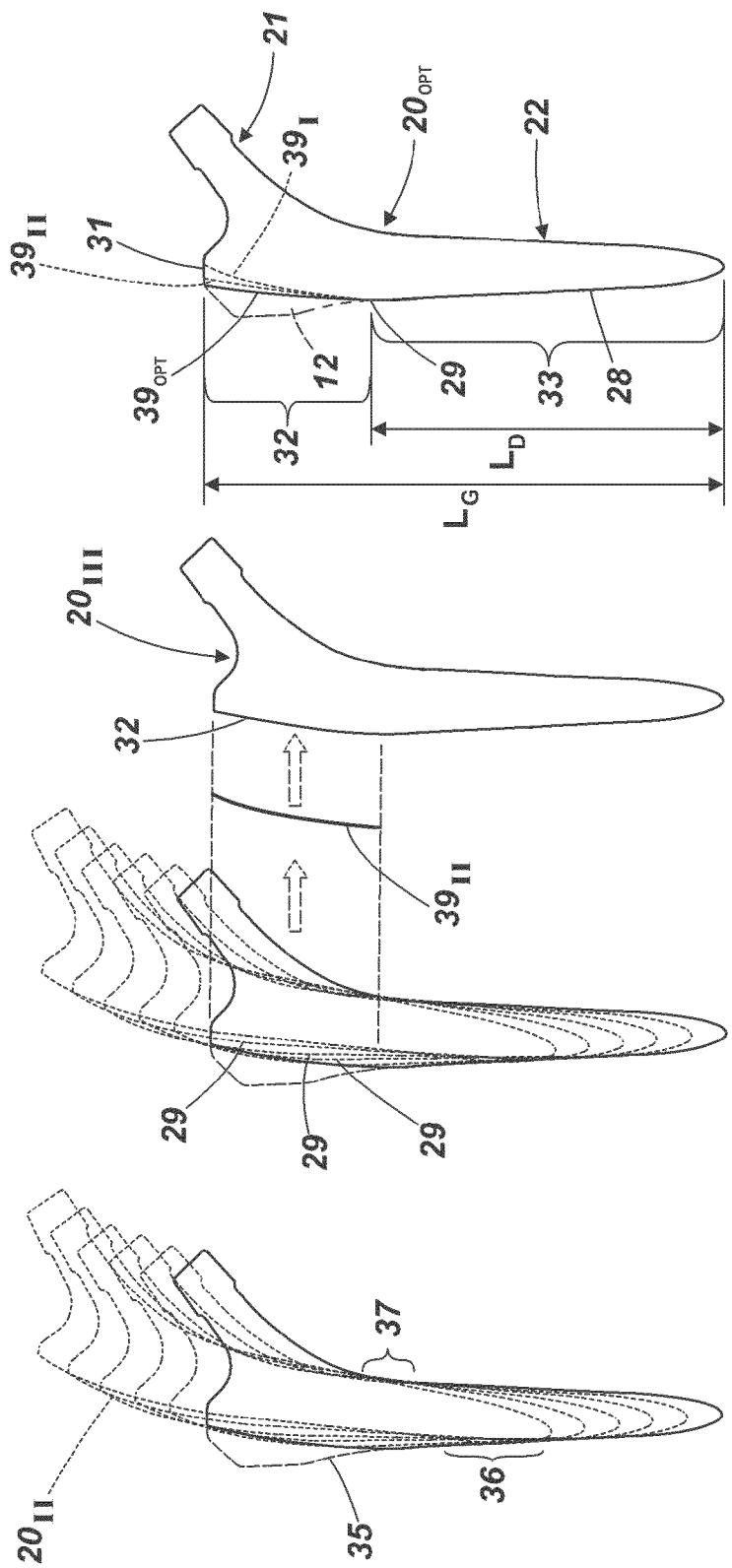

HIP-JOINT PROSTHESIS

PRIORITY INFORMATION

This application is a continuation-in-part under 35 U.S.C. §120 of U.S. patent application Ser. No. 12/067,635 (filed 15 Oct. 2008), titled "BLADE-LIKE SHAFT OF A HIP-JOINT PROSTHESIS," which is a US National Phase of the International Application No. PCT/EP2006/007842 filed Aug. 8, 2006 designating the US and published in German on Mar. 29, 2007 WO 2007/033727, which claims priority of German Patent Application No. 10 2005 044 872.0, filed Sep. 20, 2005, as well as German Patent Application No. 10 2005 048 873.0, filed Oct. 12, 2005.

BACKGROUND OF THE INVENTIONS

1. Field of the Inventions

The inventions relate to methods of optimizing the geometry of femoral stems of hip joint prostheses for implantation into a femur, femoral stems of hip joint prostheses produced by said methods and to hip joint prosthesis systems for use in the implantation of said femoral stems into a femur.

2. Description of the Related Art

A femoral stem of a hip joint prosthesis for implantation in a femur comprises a neck and an anchoring portion in the form of an anchoring blade that tapers towards a distal end. Such stems are known, for example as described in U.S. Pat. No. 4,908,035, which is incorporated by reference herein in its entirety. In order to implant such a stem during surgery, the hip joint is opened and the neck of the femur is resectioned. The proximal femur is then prepared for receiving the anchoring blade. This preparation involves the creation of a bony anchoring bed within the proximal femur by using suitable shaping instruments, in particular one or more appropriately shaped rasps. Each rasp is usually hammered down into the medullary space of the femur that is filled with spongy bone and soft tissue in order to scrape or rub away the bone so that ultimately an anchoring bed is produced that conforms in shape to the shape of the anchoring blade of the prosthesis stem. If the stem is to be implanted by cementless anchoring, then the blade of the stem is preferably straight, as described in U.S. Pat. No. 4,908,035. In this case, as shown in FIG. 1, the anchoring bed of the femur 1 requires the medullary space 2 to be opened not only in the plane 3 of the resection surface of the neck of the femur 1, but also further laterally into the region of the greater trochanter 4 to provide an axial anchoring bed for the anchoring blade.

While such implantation techniques produce a stable joint with good bone ingrowth behaviour after implantation, they also involve resections and detachments of tendon and muscle insertions in the region of the greater trochanter 4. This necessarily involves significant operative trauma, particularly to functionally significant structures such as the tendons and muscles as good operation of the hip joint after such surgery relies on the functionability of these muscles and tendons.

More recently, there has been an increase in hip prostheses using minimally invasive surgical techniques. The aim of such techniques is a more a rapid rehabilitation of the patient, which is associated with a reduction in pain and a shorter stay in hospital. Such minimally invasive surgical techniques try to avoid resections of tendons and muscles in the region of the greater trochanter 4. This usually means that instead of producing an anchoring bed as shown in FIG. 1, a bed is produced similar to that shown in FIG. 2, wherein it can be seen that the greater trochanter 4 is left substantially undisturbed, the medullary space 2 being opened in the plane 3 of the resection surface and the greater trochanter 4 being undercut, as at an undercut profile 5 in a proximal lateral region of the space. This creates an anchoring bed into which a femoral stem of a hip joint prosthesis stem must be implanted that is substantially axial over the greater part of its length but that has a slightly curved or angled proximal portion. In such a stem some or all of a trochanter wing of a blade of the stem has to be omitted. An embodiment of such a femoral stem 6 of a hip joint prosthesis is shown in FIG. 3 and is described in US Pat. App. Pub. No. 2009/0036994, which is incorporated by reference herein in its entirety. The aim of this shape of prosthesis is to provide an anchoring blade suitable for implantation by minimally invasive surgical techniques while retaining as far as possible the advantages of conventional straight stem implants.

SUMMARY OF THE INVENTIONS

With reference to FIG. 3, the femoral stem 6 comprises a neck 7 and an anchoring blade 8 which tapers towards a distal end 9. The lateral narrow side of the distal end 9 comprises a distal straight portion 10 and a proximal arcuate portion 11, the straight portion 10 extending over a length $L_D$ that is between 60% to 75% of the total length $L_G$ of the blade 8. The lateral straight portion 10 may merge continuously into the lateral arcuate portion 11, that is to say it is tangential, as shown in FIG. 3 or this transition may comprise a discontinuity, that is to say to be obtuse-angled. Shown in dotted lines 12 is a trochanter wing that is present in many prior art prostheses but which is omitted in this case.

It will be appreciated that in order to obtain the maximum benefit from a minimally invasive surgical technique, as much bone as possible should be preserved in the region of the greater trochanter 4 and the proximal arcuate portion 11 of the stem 6 shown in FIG. 3 should be of a complementary shape to the undercut profile 5 of the anchoring bed so that there are no gaps between the blade 8 and the bed. Although bone tissue is able to grow into minor gaps of a width up to 0.2 mm, larger gaps cannot be bridged. Here lyse edges many form that lead to loosening of the prosthesis. Hence, it is important that the anchoring bed is shaped using rasps of increasing size up to a size giving the best fit of the blade 8 into the bed. Conventionally, this is influenced by a surgeon's rasp technique and individual bone quality.

One embodiment of the inventions provides a method of optimizing the geometry of an anchoring blade of a femoral stem of a hip joint prosthesis such as is shown in FIG. 3 to provide an optimal fit between the blade and the anchoring bed.

A further embodiment provides a hip joint prosthesis system for use in the implantation of said anchoring blade into a femur that optimizes the fit between the blade and the anchoring bed.

According to another embodiment there is provided a method of optimizing the geometry of a femoral stem of a hip joint prosthesis, the femoral stem comprising a neck; and an anchoring blade that is attached to the neck and that tapers towards a distal end with a lateral narrow side comprising a distal straight portion and a proximal arcuate portion corresponding to a curve, a transition between the distal straight portion and said proximal arcuate portion occurring at an outer lateral point; and said method comprising a means of optimizing the profile of the curve of said proximal arcuate portion by a process of iterative modeling steps using a series of curves each defined by a path traced by the outer lateral point of the blade on withdrawal of a profile of the stem from a cavity of complementary shape to the stem.

In further embodiments, during withdrawal of the profile of the stem from the cavity contact between lateral-distal and proximal-medial stem contours and respective associated boundaries of the cavity are maintained.

Also in even further embodiments, in a first iterative step a first curve is defined by a path traced by the outer lateral point passing to the medial side of an arbitrarily selected proximal point on a part of the blade adjacent the neck on withdrawal of a profile of the stem from the cavity of complementary shape to the stem while contact between lateral-distal and proximal-medial stem contours and respective associated boundaries of the cavity are maintained; in a plurality of further iterative steps the curve defined in the preceding iterative step is used as the profile of the proximal arcuate portion of the stem, and a new curve is then defined by the path traced by the outer lateral point on withdrawal of the stem with this profile from the original cavity while contact between lateral-distal and proximal-medial stem contours and respective associated boundaries of the cavity are maintained; and the new curve defined by the path traced by the outer lateral point in the final iterative step is adopted as the profile of the proximal arcuate portion of the anchoring blade of the femoral stem.

According to another embodiment there is provided a femoral stem of a hip joint prosthesis with a geometry optimized in accordance with the method of the first aspect of the invention.

According to a third embodiment there is provided a hip joint prosthesis system for use in the implantation of a femoral stem into a femur comprising a femoral stem with a geometry optimized in accordance with the methods described above and a rasp configured for forming a cavity in a femur and defining a proximal arcuate portion with a profile that conforms to a proximal arcuate portion of an anchoring blade of the femoral stem.

It should be appreciated that whereas conventionally the shape of the anchoring bed in the femur is profiled by the surgeon to fit the shape of the femur anchoring portion of the prosthesis, some embodiments of the present invention can be predicated on the profile of the proximal arcuate portion being defined by the curve produced by the largest of a series of rasps. In other words, the curve produced by the rasp can define the shape of the prosthesis rather than vice versa.

BRIEF DESCRIPTION OF THE DRAWINGS

The various aspects of the present invention will now be described by way of example with reference to the accompanying drawing in which:

FIG. 1 is a diagram showing schematically a longitudinal sectional view of a resected head of a femur prior to implantation of a stem of a prior art hip joint prosthesis;

FIG. 2 is a diagram similar to FIG. 1 but of a resected head of a femur prior to implantation of a stem of another hip joint prosthesis;

FIGS. 4a to 4d depict a sequence showing diagrammatically a first iterative step to optimize the geometry of the profile of the femoral stem shown in FIG. 3;

FIGS. 5a to 5c form a sequence showing diagrammatically a second iterative step that follows a sequence similar to that shown in FIGS. 4a to 4d;

FIG. 6 is a side view showing the profile of a femoral stem of a hip joint prosthesis optimized in accordance with the present invention.

DETAILED DESCRIPTION OF THE PREFERRED EMBODIMENTS

Figure 3:
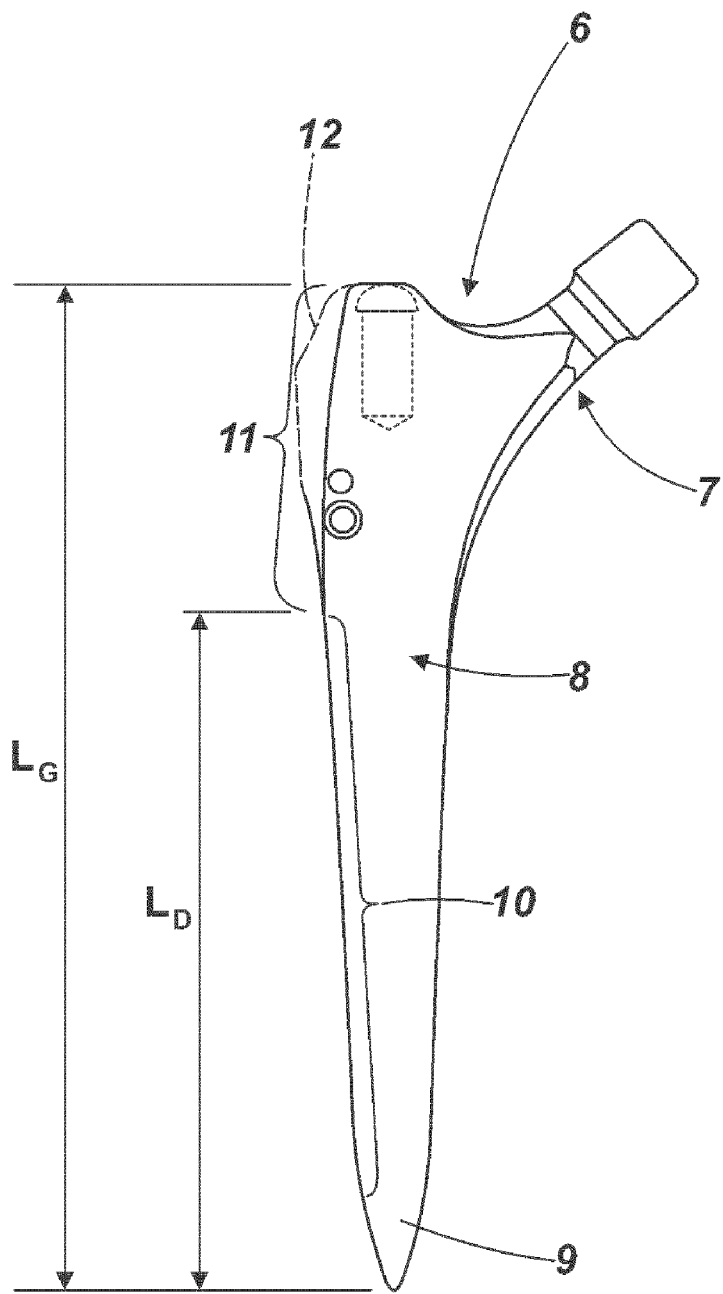
FIG. 3 is a side view of a femoral stem of a hip joint prosthesis known in the prior art.

An iterative method of optimizing the geometry of a femoral stem of a hip joint prosthesis can start using a femoral stem 20 of conventional shape that is based on the proximal part of an average femur determined via X-ray photography or equivalent techniques. The profile of one such stem 20 is shown in FIG. 4a and comprises a neck 21 and an anchoring blade 22 that tapers towards a distal end 23. The blade 22 can widen on all sides from the distal end 23 in the direction of the proximal end. In another embodiment, the blade 22 can widen in the medial-lateral direction but have a generally flat anterior and/or posterior surface. A medial narrow side 24 merges out of this cone into a continuously curved arc 25 which ends in a plane that, running perpendicular to the neck axis 26, terminates the neck 21 on the side of the blade 22. The neck 21 is itself terminated by an outwardly conically tapering pin 27 on which a spherical joint head (not shown) can be located. On the opposite side of the blade 22 the lateral narrow side 28 widens out of the cone to a lateral point 29 and then defines a trochanter wing 30 before merging, via a shoulder 31 into the neck termination plane.

The cross-sectional profile of the blade 22 is preferably rectangular, but may also be trapezoidal or rhombic. The widening part of the blade 22 preferably has a taper angle of from 0.5° to 6° and especially an angle of from 1° to 3°, particularly on the ventral and/or dorsal side of the stem 22.

In one embodiment, the optimization method can include removing some or all of the trochanter wing 30 to provide a proximal arcuate portion 32 (see FIG. 4d) with a profile corresponding to an optimized curve, such as that shown in FIG. 6. In that embodiment the arcuate portion 32 extends from the lateral point 29 to the shoulder 31. The lateral point 29 can be located at the level of the metaphysis so that the lateral point 29 is at a lateral metaphyseal point of the blade 22. The lateral narrow side 28 of the stem 20 can have a distal straight portion 33 which extends over a length of from 60% to 75% of the total length of said stem 20.

In some embodiments, the iterative steps of the methods described herein can be performed as simulations on a computer, using motion-simulation software that is generally understood in the art. A first iterative step can involve modeling the profile of the stem 20 as shown in FIG. 4a and defining the position of the point 29. A proximal point 34 can then be arbitrarily selected on a part of the shoulder 31 adjacent the neck 21. This arbitrarily selected point 34 can define a first arbitrary position of a proximal end of the arcuate portion 32 and thereby define a first profile $20_I$. The modeling process is intended to refine this position. The profile $20_I$ of the stem 20 is now withdrawn from a cavity 35 of complementary shape to the stem 20, as shown in FIGS. 4b and 4c. During the withdrawal the lateral point 29 can be forced to pass to the medial side of the proximal point 34, while contact is maintained between the blade 22 and the cavity 35, and in particular between a lateral-distal contour 36 and a proximal-medial stem contour 37 of the blade 22 and respective associated boundaries of the cavity 35. This can then imitate the path of a rasp that would be used during surgery to make the cavity 35 in a femur.

The path 38 of the lateral point 29 is traced (e.g., using computer graphics) and is seen to define a curve $39_I$. This curve $39_I$ is a first approximation to the optimized shape of the proximal arcuate portion 32 being modeled. This curve $39_I$ can then provide the profile of the portion 32 of a stem $20_{II}$, as shown in FIG. 4d that is used in a second iteration of the method as shown in FIGS. 5a to 5c.

In the second iteration, a profile of the stem $20_{II}$ can again be withdrawn from the cavity 35 whilst contact is maintained between the lateral-distal contour 36 and the proximal-medial stem contour 37 of the blade 22 and the respective associated boundaries of the cavity 35. The path of the lateral point 29 is again traced and this time defines a new curve $39_{II}$.

The new curve $39_{II}$ can then provide the profile $20_{III}$ of the portion 32 of a stem $20_{III}$, as shown in FIG. 5c that can then be used in a third iteration of the method, which is identical to the second iteration as described above. In some embodiments at least five iterations can be performed. Further, in some embodiments at least seven iterations can be performed. Each time, the curve $39_N$ (where N is the iteration step) used for the profile of the portion 32 is that defined in the previous iteration step. It has been found that after between five to seven iterations the position and profile of the curve 39 will often no longer discernibly change and an optimal curve $39_{OPT}$ has been found. This curve $39_{OPT}$ is then used to provide an optimal profile for the proximal arcuate portion 32 of the anchoring blade 22 of a stem $20_{OPT}$. This profile $39_{OPT}$ is shown in solid lines in FIG. 6, which also shows in dotted lines the profiles formed by the curves $39_I$ and $39_{II}$ produced after the first and second iterations, respectively, as well as the trochanter wing 12 which has been removed from the profile.

Figure 7:
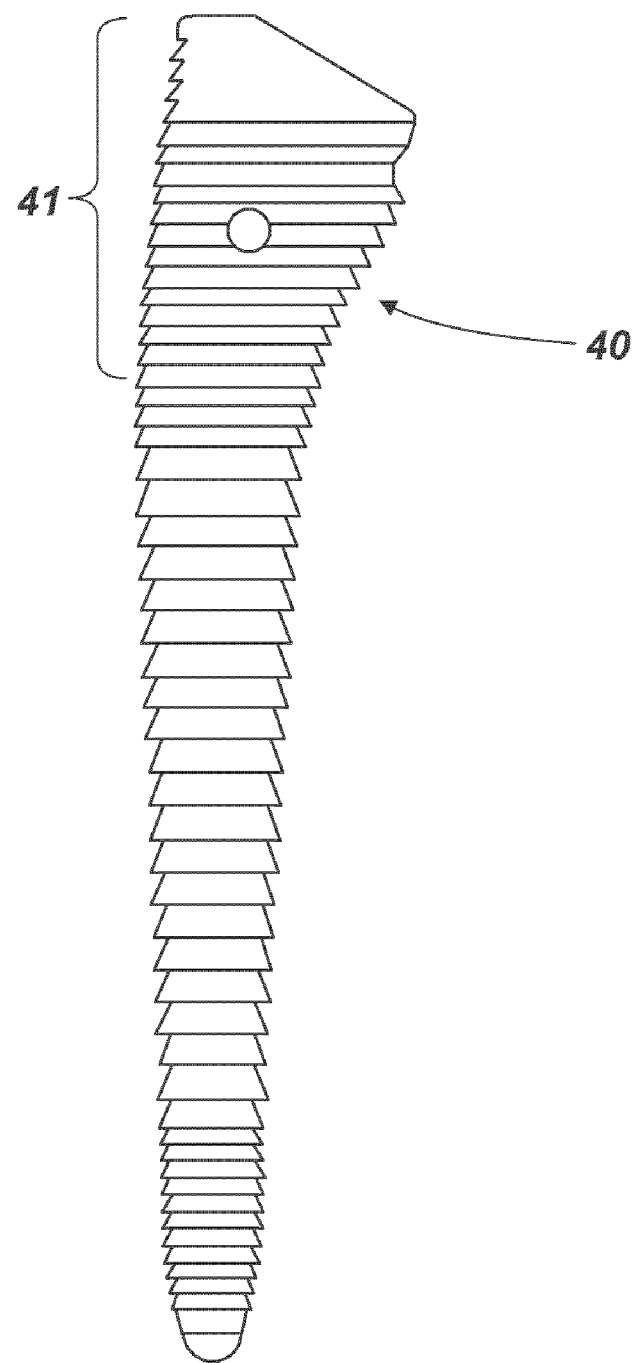
FIG. 7 is a diagram showing a rasp with a profile that conforms to the profile of the femoral stem shown in FIG. 6.

As previously mentioned, the optimal profile $39_{OPT}$ of the proximal arcuate portion can be based on the curve that can be produced by a rasp in order to ensure an optimal fit of the blade. An embodiment of such a rasp 40 is shown in FIG. 7. This rasp 40 is configured for forming a cavity in a femur and defines a proximal arcuate portion 41 with a profile that conforms to the optimal profile $39_{OPT}$ of the blade 22. Further, the whole of the profile of the rasp 40 can be configured for forming a cavity in a femur having exactly the same configuration as the blade 22 of the optimal stem $20_{OPT}$.

During surgery, the anchoring bed in a femur can be shaped using a series of rasps of increasing size up to the size of rasp giving the best fit. Each rasp in the series can follow the shape of the bed formed by the preceding rasp size. Advantageously, therefore, the rasp 40 can form one of a series of rasps of increasing size and all of the rasps in the series can have a configuration with relative dimensions the same as the relative dimensions as the rasp 40. Hence, during surgery the surgeon starts off shaping the anchoring bed in a resected femur by using the first and smallest rasp of the series and gradually increases the size of rasp being used until the anchoring bed is the size required. For example, although a series of rasps of sizes from 1, the smallest, to 7, the largest, may be provided, if a stem 20 is to be fitted of size 5, then the surgeon only needs to use rasps 1 to 5 to produce an anchoring bed of the correct size. There is thus achieved an optimum fit of the blade 22 with the anchoring bed, either with gap-free seating or with an exact, predetermined gap for cement, according to whether a cementless or cemented implantation is to be carried out. It will be appreciated in the latter case that the rasps used can be slightly larger, in proportion, than the sizes of the stems 20 to leave room for the cement when the blade 22 is inserted into the anchoring bed.

What is claimed is:

1. A method of optimizing the geometry of a femoral stem of a hip joint prosthesis, the femoral stem comprising a neck; and an anchoring blade that is attached to the neck and that tapers towards a distal end with a lateral narrow side comprising a distal straight portion and a proximal arcuate portion corresponding to a curve, a transition between the distal straight portion and said proximal arcuate portion occurring at an outer lateral point; and said method comprising optimizing the profile of the curve of said proximal arcuate portion by a process of iterative modeling steps using a series of curves each defined by a path traced by the outer lateral point of the blade on withdrawal of a profile of the stem from a cavity of complementary shape to the stem.

2. A method as claimed in claim 1, wherein the outer lateral point coincides with a lateral metaphyseal point.

3. A method as claimed in claim 1, wherein during withdrawal of the profile of the stem from the cavity contact between lateral-distal and proximal-medial stem contours and respective associated boundaries of the cavity are maintained.

4. A method as claimed in claim 1, wherein in a first iterative step a first curve is defined by a path traced by the outer lateral point passing to the medial side of an arbitrarily selected proximal point on a part of the blade adjacent the neck on withdrawal of a profile of the stem from the cavity of complementary shape to the stem while contact between lateral-distal and proximal-medial stem contours and respective associated boundaries of the cavity are maintained, and that curve is used as the profile of the proximal arcuate portion of the stem in a next iterative step.

5. A method as claimed in claim 4, wherein in a plurality of further iterative steps the curve defined in the preceding iterative step is used as the profile of the proximal arcuate portion of the stem, and a new curve is then defined by the path traced by the outer lateral point on withdrawal of the stem with this profile from the original cavity while contact between lateral-distal and proximal-medial stem contours and respective associated boundaries of the cavity are maintained.

6. A method as claimed in claim 5, wherein the new curve defined by the path traced by the outer lateral point in the final iterative step is adopted as the profile of the proximal arcuate portion of the anchoring blade of the femoral stem.

7. A method as claimed in claim 1, wherein at least five iterative steps are carried out to determine the profile of the proximal curve of said proximal arcuate portion of the prosthesis stem.

8. A method as claimed in claim 1, wherein at least seven iterative steps are carried out to determine the profile of the proximal curve of said proximal arcuate portion of the prosthesis stem.

9. A method as claimed in claim 1, wherein the distal straight portion of the blade extends over a length of from 60% to 75% inclusive of the total length of the femoral stem.

10. A method as claimed in claim 1, wherein the cross-sectional profile of the blade is selected from the group consisting of rectangular, trapezoidal and rhombic.

11. A method as claimed in claim 1, wherein the blade tapers with a taper angle of from 0.5° to 6°.

12. A method as claimed in claim 1, wherein the blade tapers with a taper angle of from 1° to 3°.

13. A method of optimizing the geometry of a femoral stem of a hip joint prosthesis, the femoral stem comprising a neck; and an anchoring blade that is attached to the neck and that tapers towards a distal end with a lateral narrow side comprising a distal straight portion and a proximal arcuate portion corresponding to a curve, a transition between the distal straight portion and said proximal arcuate portion occurring at an outer lateral point; and said method comprising optimizing the profile of the curve of said proximal arcuate portion by a process of iterative modeling steps using a series of curves each defined by a path traced by the outer lateral point of the blade on withdrawal of a profile of the stem from a cavity of complementary shape to the stem;

wherein the outer lateral point coincides with a lateral metaphyseal point; and wherein during withdrawal of the profile of the stem from the cavity contact between lateral-distal and proximal-medial stem contours and respective associated boundaries of the cavity are maintained.

14. A method of optimizing the geometry of a femoral stem of a hip joint prosthesis, the femoral stem comprising a neck; and an anchoring blade that is attached to the neck and that tapers towards a distal end with a lateral narrow side comprising a distal straight portion and a proximal arcuate portion corresponding to a curve, a transition between the distal straight portion and said proximal arcuate portion occurring at an outer lateral point; and said method comprising a means of optimizing the profile of the curve of said proximal arcuate portion by a process of iterative modeling steps using a series of curves each defined by a path traced by the outer lateral point of the blade on withdrawal of a profile of the stem from a cavity of complementary shape to the stem.

15. A method as claimed in claim 14, wherein in a first iterative step a first curve is defined by a path traced by the outer lateral point passing to the medial side of an arbitrarily selected proximal point on a part of the blade adjacent the neck on withdrawal of a profile of the stem from the cavity of complementary shape to the stem while contact between lateral-distal and proximal-medial stem contours and respective associated boundaries of the cavity are maintained, and that curve is used as the profile of the proximal arcuate portion of the stem in a next iterative step.

* * * * *